(12) United States Patent
Quiles (10) Patent No.: US 8,494,647 B2
(45) Date of Patent: Jul. 23, 2013

(54) SECURE REMOTE ACCESS FOR AN IMPLANTABLE MEDICAL DEVICE

(75) Inventor: Sylvia Quiles, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 107 days.

(21) Appl. No.: 12/986,333

(22) Filed: Jan. 7, 2011

(65) Prior Publication Data

US 2011/0098788 A1 Apr. 28, 2011

Related U.S. Application Data

(62) Division of application No. 10/914,641, filed on Aug. 9, 2004, now Pat. No. 7,890,180.

(51) Int. Cl.
*A61N 1/08* (2006.01)

(52) U.S. Cl.
USPC ............................................. 607/60; 607/31

(58) Field of Classification Search
USPC ............................................. 607/30, 31, 60
See application file for complete search history.

(56) References Cited

U.S. PATENT DOCUMENTS

| | | | |
|---|---|---|---|
| 3,914,586 A | 10/1975 | McIntosh | |
| 4,404,972 A | 9/1983 | Gordon et al. | |
| 4,486,739 A | 12/1984 | Franaszek et al. | |
| 4,539,992 A | 9/1985 | Calfee et al. | |
| 4,562,841 A | 1/1986 | Brockway et al. | |
| 4,613,937 A | 9/1986 | Batty, Jr. | |
| 5,074,308 A | 12/1991 | Sholder et al. | |
| 5,080,096 A | 1/1992 | Hooper et al. | |
| 5,230,003 A | 7/1993 | Dent et al. | |
| 5,456,692 A | 10/1995 | Smith, Jr. et al. | |
| 5,630,835 A | 5/1997 | Brownlee | |
| 5,683,432 A | 11/1997 | Goedeke et al. | |
| 5,694,952 A | 12/1997 | Lidman et al. | |
| 5,725,559 A | 3/1998 | Alt et al. | |
| 5,737,419 A | 4/1998 | Ganesan | |
| 5,807,397 A | 9/1998 | Barreras | |
| 5,843,139 A | 12/1998 | Goedeke et al. | |
| 5,898,397 A | 4/1999 | Murray | |
| 6,028,527 A | 2/2000 | Soenen et al. | |
| 6,044,485 A | 3/2000 | Dent et al. | |
| 6,169,925 B1 | 1/2001 | Villaseca et al. | |

(Continued)

FOREIGN PATENT DOCUMENTS

| JP | 2001251451 A | 9/2001 |
|---|---|---|
| JP | 2001-274901 A | 10/2001 |

(Continued)

OTHER PUBLICATIONS

"", Wikipedia, SHA hash functions: http://en.wikipedia.org/wiki/SHA, (1993), 8 pgs.

(Continued)

*Primary Examiner* — Eric D. Bertram (74) *Attorney, Agent, or Firm* — Schwegman Lundberg & Woessner, P.A.

(57) ABSTRACT

This document discloses, among other things, a telemetry system that controls access to assets of an implantable device as a function of the manner of initiating the communication session or an access code. A tiered hierarchy of assets are associated with corresponding levels of access. A tiered array of security mechanisms are associated with the hierarchy of assets.

20 Claims, 7 Drawing Sheets

U.S. PATENT DOCUMENTS

| | | | |
|---|---|---|---|
| 6,223,083 B1 | 4/2001 | Rosar | |
| 6,336,900 B1 | 1/2002 | Alleckson et al. | |
| 6,385,318 B1 | 5/2002 | Oishi | |
| 6,424,867 B1* | 7/2002 | Snell et al. | 607/31 |
| 6,434,429 B1 | 8/2002 | Kraus et al. | |
| 6,443,891 B1 | 9/2002 | Grevious | |
| 6,463,329 B1 | 10/2002 | Goedeke | |
| 6,470,215 B1 | 10/2002 | Kraus et al. | |
| 6,490,487 B1 | 12/2002 | Kraus et al. | |
| 6,535,766 B1 | 3/2003 | Thompson et al. | |
| 6,562,001 B2 | 5/2003 | Lebel et al. | |
| 6,564,104 B2 | 5/2003 | Nelson et al. | |
| 6,564,105 B2 | 5/2003 | Starkweather et al. | |
| 6,567,793 B1 | 5/2003 | Hicks et al. | |
| 6,574,510 B2 | 6/2003 | Von Arx et al. | |
| 6,600,952 B1 | 7/2003 | Snell et al. | |
| 6,602,191 B2 | 8/2003 | Quy | |
| 6,622,050 B2 | 9/2003 | Thompson | |
| 6,687,546 B2 | 2/2004 | Lebel et al. | |
| 6,907,291 B1 | 6/2005 | Snell et al. | |
| 6,970,735 B2 | 11/2005 | Uber, III et al. | |
| 6,985,088 B2 | 1/2006 | Goetz et al. | |
| 7,110,784 B2 | 9/2006 | Nasu et al. | |
| 7,155,290 B2 | 12/2006 | Von Arx et al. | |
| 7,228,182 B2 | 6/2007 | Healy et al. | |
| 7,274,642 B2 | 9/2007 | Sako et al. | |
| 7,406,349 B2 | 7/2008 | Seeberger et al. | |
| 7,475,245 B1 | 1/2009 | Healy et al. | |
| 7,818,067 B2 | 10/2010 | Healy et al. | |
| 7,890,180 B2 | 2/2011 | Quiles | |
| 2001/0001014 A1 | 5/2001 | Akins et al. | |
| 2001/0019614 A1 | 9/2001 | Madoukh | |
| 2001/0027331 A1* | 10/2001 | Thompson | 607/60 |
| 2002/0032661 A1 | 3/2002 | Schuba et al. | |
| 2002/0046276 A1 | 4/2002 | Coffey et al. | |
| 2002/0062139 A1 | 5/2002 | Ding | |
| 2002/0115912 A1 | 8/2002 | Muraki et al. | |
| 2002/0120838 A1 | 8/2002 | Abdulkader | |
| 2002/0143372 A1 | 10/2002 | Snell et al. | |
| 2002/0147388 A1 | 10/2002 | Mass et al. | |
| 2003/0050535 A1 | 3/2003 | Bowman, IV et al. | |
| 2003/0065919 A1 | 4/2003 | Albert et al. | |
| 2003/0074036 A1 | 4/2003 | Prutchi et al. | |
| 2003/0083719 A1 | 5/2003 | Shankar et al. | |
| 2003/0114897 A1 | 6/2003 | Von Arx et al. | |
| 2003/0114898 A1 | 6/2003 | Von Arx et al. | |
| 2003/0159048 A1 | 8/2003 | Matsumoto et al. | |
| 2003/0174069 A1 | 9/2003 | Goetz et al. | |
| 2004/0009815 A1 | 1/2004 | Zotto et al. | |
| 2004/0030260 A1 | 2/2004 | Von Arx | |
| 2004/0047434 A1 | 3/2004 | Waltho | |
| 2004/0122489 A1 | 6/2004 | Mazar et al. | |
| 2004/0168071 A1 | 8/2004 | Silverbrook | |
| 2004/0260363 A1 | 12/2004 | Arx et al. | |
| 2005/0203582 A1 | 9/2005 | Healy et al. | |
| 2005/0204134 A1 | 9/2005 | Von Arx et al. | |
| 2005/0261934 A1 | 11/2005 | Thompson | |
| 2005/0288736 A1 | 12/2005 | Persen et al. | |
| 2006/0029100 A1 | 2/2006 | Dove | |
| 2006/0030903 A1 | 2/2006 | Seeberger et al. | |
| 2006/0030904 A1 | 2/2006 | Quiles | |
| 2007/0100396 A1 | 5/2007 | Freeberg | |
| 2007/0118188 A1 | 5/2007 | Von Arx et al. | |
| 2007/0135216 A1 | 6/2007 | Martinek et al. | |
| 2007/0169181 A1 | 7/2007 | Roskind | |
| 2007/0260293 A1 | 11/2007 | Carpenter et al. | |
| 2007/0282398 A1 | 12/2007 | Healy et al. | |
| 2008/0046745 A1 | 2/2008 | Buch et al. | |
| 2008/0262573 A1 | 10/2008 | Seeberger et al. | |

FOREIGN PATENT DOCUMENTS

| | | |
|---|---|---|
| JP | 2001285337 A | 10/2001 |
| JP | 2002112347 A | 4/2002 |
| JP | 2002-132962 A | 5/2002 |
| JP | 2003-022008 | 1/2003 |
| JP | 2003299150 A | 10/2003 |
| JP | 2003348228 A | 12/2003 |
| JP | 2004-094544 A | 3/2004 |
| JP | 2004104774 A | 4/2004 |
| JP | 2005281027 A | 10/2005 |
| WO | WO-2005000397 A1 | 1/2005 |
| WO | WO-2005091546 A2 | 9/2005 |
| WO | WO-2005091546 A3 | 9/2005 |
| WO | WO-2006020546 A1 | 2/2006 |

OTHER PUBLICATIONS

"U.S. Appl. No. 10/601,763, Non Final Office Action mailed Feb. 23, 2006", 9 pgs.

"U.S. Appl. No. 10/601,763, Notice of Allowance mailed Aug. 4, 2006", 8 pgs.

"U.S. Appl. No. 10/601,763, Response filed May 23, 2006 to Non-Final Office Action mailed Feb. 23, 2006", 13 pgs.

"U.S. Appl. No. 10/601,763, Supplemental Notice of Allowability mailed Oct. 23, 2006", 4 pgs.

"U.S. Appl. No. 10/801,070, Amendment Under 37 CFR 1.312 filed Apr. 11, 2007", 4 pgs.

"U.S. Appl. No. 10/801,070, Non-Final Office Action mailed Feb. 6, 2006", 17 pgs.

"U.S. Appl. No. 10/801,070, Non-Final Office Action mailed Jun. 16, 2006", 6 pgs.

"U.S. Appl. No. 10/801,070, Notice of Allowance dated Jan. 12, 2007", 7 pgs.

"U.S. Appl. No. 10/801,070, Response filed Mar. 7, 2006 to Non-Final Office Action mailed Feb. 6, 2006", 10 pgs.

"U.S. Appl. No. 10/801,070, Response filed Sep. 18, 2006 to Non Final Office Action mailed Jun. 16, 2006", 11 pgs.

"U.S. Appl. No. 10/801,070, Response filed Sep. 18, 2006 to Non-Final Office Action", 15 pgs.

"U.S. Appl. No. 10/870,324, Advisory Action mailed Mar. 21, 2008", 3 pgs.

"U.S. Appl. No. 10/870,324, Final Office Action mailed Jan. 8, 2008", 8 pgs.

"U.S. Appl. No. 10/870,324, Non Final Office Action mailed Jun. 27, 2007", 6 pgs.

"U.S. Appl. No. 10/870,324, Response filed Feb. 8, 2008 to Final Office Action mailed Jan. 8, 2008", 20 pgs.

"U.S. Appl. No. 10/870,324, Response filed Oct. 29, 2007 to Non-Final Office Action mailed Jun. 27, 2007", 21 pgs.

"U.S. Appl. No. 10/914,499, Non-Final Office Action mailed May 29, 2007", 11 pgs.

"U.S. Appl. No. 10/914,638, Final Office Action mailed Apr. 17, 2007", 10 pgs.

"U.S. Appl. No. 10/914,638, Non-Final Office Action mailed Oct. 18, 2006", 9 pgs.

"U.S. Appl. No. 10/914,638, Notice of Allowance mailed Mar. 21, 2008", 4 pgs.

"U.S. Appl. No. 10/914,638, Notice of Allowance mailed Oct. 22, 2007", 4 pgs.

"U.S. Appl. No. 10/914,638, Response filed Jan. 18, 2007 to Non-Final Office Action mailed Oct. 18, 2006", 16 pgs.

"U.S. Appl. No. 10/914,638, Response filed Aug. 17, 2007 to Final Office Action mailed Apr. 17, 2007", 8 pgs.

"U.S. Appl. No. 10/914,641, Final Office Action dated Apr. 17, 2007", 10 pgs.

"U.S. Appl. No. 10/914,641, Final Office Action mailed Mar. 10, 2009", 10 pgs.

"U.S. Appl. No. 10/914,641, Final Office Action mailed Mar. 11, 2010", 11 pgs.

"U.S. Appl. No. 10/914,641, Final Office Action mailed Feb. 20, 2008", 9 pgs.

"U.S. Appl. No. 10/914,641, Final office action mailed Mar. 15, 2007", 10 pgs.

"U.S. Appl. No. 10/914,641, Non-Final Office Action mailed Aug. 18, 2009", 11 pgs.

"U.S. Appl. No. 10/914,641, Non-Final Office Action Mailed Aug. 31, 2007", 9 pgs.

"U.S. Appl. No. 10/914,641, Non-Final Office Action mailed Aug. 22, 2008", 9 pgs.

"U.S. Appl. No. 10/914,641, Non-Final Office Action mailed Aug. 2, 2006", 9 pgs.

"U.S. Appl. No. 10/914,641, Notice of Allowance mailed Aug. 4, 2006", 8 pgs.

"U.S. Appl. No. 10/914,641, Response filed Jan. 2, 2007 Non-Final Office Action mailed Aug. 2, 2006", 9 pgs.

"U.S. Appl. No. 10/914,641, Response filed May 11, 2009 to Final Office Action mailed Mar. 10, 2009", 12 pgs.

"U.S. Appl. No. 10/914,641, Response filed May 18, 2010 to Final Office Action mailed Mar. 11, 2010", 11 pgs.

"U.S. Appl. No. 10/914,641, Response filed Jun. 10, 2009 to Advisory Action mailed Mar. 10, 2009", 11 pgs.

"U.S. Appl. No. 10/914,641, Response filed Nov. 18, 2009 to Non Final Office Action mailed Aug. 18, 2009", 11 pgs.

"U.S. Appl. No. 10/914,641, Response filed Nov. 30, 2007 to Non-Final Office Action mailed Aug. 31, 2007", 14 pgs.

"U.S. Appl. No. 10/914,641, Response filed Nov. 24, 2008 to Non-Final Office Action mailed Aug. 22, 2008", 11 pgs.

"U.S. Appl. No. 10/914,641, Response filed Jun. 16, 2006 to Restriction Requirement mailed May 16, 2006", 5 pgs.

"U.S. Appl. No. 10/914,641, Response filed Jul. 16, 2007 Final Office Action mailed Mar. 15, 2007", 9 pgs.

"U.S. Appl. No. 10/914,641, Response to Final Office Action filed Jul. 16, 2007", 9 pgs.

"U.S. Appl. No. 10/914,641, Restriction Requirement mailed Mar. 16, 2006", 5 pgs.

"U.S. Appl. No. 11/640,552, Examiner Interview Summary Received May 27, 2010", 4 pgs.

"U.S. Appl. No. 11/640,552, Examiner Interview Summary Received Aug. 10, 2009", 3 pgs.

"U.S. Appl. No. 11/640,552, Final Office Action mailed Mar. 24, 2010", 8 pgs.

"U.S. Appl. No. 11/640,552, Non-Final Office Action mailed May 11, 2009", 8 pgs.

"U.S. Appl. No. 11/640,552, Response filed Jun. 24, 2010 to Final Office Action mailed Mar. 24, 2010", 9 pgs.

"U.S. Appl. No. 11/640,552, Response filed Aug. 11, 2009 to Non-Final Office Action mailed May 11, 2009", 10 pgs.

"U.S. Appl. No. 11/738,942, Non-Final Office Action mailed Jan. 20, 2010", 8 pgs.

"U.S. Appl. No. 11/738,942, Non-Final Office Action mailed Jun. 9, 2009", 14 pgs.

"U.S. Appl. No. 11/738,942, Notice of Allowance mailed Jun. 17, 2010", 8 pgs.

"U.S. Appl. No. 11/738,942, Preliminary Amendment filed Apr. 23, 2007", 6 pgs.

"U.S. Appl. No. 11/738,942, Response filed Apr. 20, 2010 to Non Final Office Action mailed Jan. 20, 2010", 10 pgs.

"U.S. Appl. No. 11/738,942, Response filed Sep. 16, 2009 to Non Final Office Action mailed Jun. 9, 2009", 9 pgs.

"U.S. Appl. No. 10/914,641, Notice of Allowance mailed Oct. 6, 2010", 5 pgs.

"European Application No. 05783799.9, Communication pursuant to Article 94(3) EPC mailed on Jun. 16, 2009", 3 pgs.

"International Application No. PCT/US2004/019902, International Search Report mailed Feb. 6, 2004", 4 pgs.

"International Application No. PCT/US2004/019902, Written Opinion mailed Feb. 6, 2004", 6 pgs.

"International Application No. PCT/US2005/008521, International Preliminary Report on Patentability mailed Sep. 28, 2006", 13 pgs.

"International Application No. PCT/US2005/008521, International Search Report and Written Opinion mailed Oct. 11, 2005", 19 pgs.

"International Application No. PCT/US2005/008521, International Search Report mailed Oct. 11, 2005", 19 pgs.

"International Application No. PCT/US2005/008521, Invitation to Pay Additional Fees and Partial International Search Report, mailed Jul. 29, 2005", 7 pgs.

"International Application No. PCT/US2005/028052, International Preliminary Report on Patentability mailed Feb. 22, 2007", 8 pgs.

"International Application No. PCT/US2005/028052, International Search Report and Written Opinion mailed Nov. 29, 2005", 12 pgs.

"Part III—Department of Health and Human Services, Office of the Secretary—45 CFR Part 142—Security and Electronic Signature Standards; Proposed Rule", Federal Register, 63(155), (Aug. 12, 1998), 43241-43280.

"Public Law 104-191 [H.R. 3103]—Health Insurance Portability and Accountability Act of 1996", United States Public Laws—104th Congress—2nd Session, (Aug. 21, 1996), 78 pgs.

Diffie, W., "The First Ten Years of Public-Key Cryptography", Proceedings of the IEEE, 76(5), (May 1988), 560-577.

Hammond, E., "Perspectives on Implementation of Administrative Simplification Provisions of P.L. 104-191", National Committee on Vital and Health Statistics, Subcommittee on Health Data Needs, Standards and Security, (Feb. 11, 1997), 4 pgs.

Healy, S. J., et al., "Cryptographic Authentication for Telemetry With an Implantable Medical Device", U.S. Appl. No. 10/801,070, filed Mar. 15, 2004, 38 pgs.

Healy, S. J., et al., "System and Method for Providing Secure Exchange of Sensitive Information With an Implantable Medical Device", U.S. Appl. No. 10/801,150, filed Mar. 15, 2004, 30 pgs.

Katoozi, M., et al., "On-Demand Retransmission of Data With an Implantable Medical Device", U.S. Appl. No. 10/870,328, filed Jun. 17, 2004, 30 pgs.

Quiles, S., "Secure Remote Access for an Implantable Medical Device", U.S. Appl. No. 10/914,641, filed Aug. 9, 2004, 41 pgs.

Seeberger, M., "U.S. Appl. No. 10/914,638, filed Aug. 9, 2004", 35 pgs.

Von Arx, J., et al., "System and Method for Securely Authenticating a Data Exchange Session With an Implantable Medical Device", U.S. Appl. No. 10/800,806, filed Mar. 15, 2004, 47 pgs.

"U.S. Appl. No. 12/145,343, Final Office Action mailed Mar. 8, 2011", 9 pgs.

"U.S. Appl. No. 12/145,343, Response filed Jan. 25, 2011 to Non Final Office Action Oct. 26, 2010", 9 pgs.

"U.S. Appl. No. 12/145,343, Response filed May 9, 2011 to Final Office Action mailed Mar. 8, 2011", 9 pgs.

"Japanese Application Serial No. 2007-525695, Office Action mailed Feb. 3, 2011", (w/ English Translation), 5 pgs.

"Japanese Application Serial No. 2007-525695, Response filed Apr. 20, 2011 to Non Final Office Action mailed Feb. 3, 2011", (w/ English Translation of Amended Claims), 10 pgs.

"U.S. Appl. No. 12/145,343, Examiner Interview Summary mailed Apr. 12, 2012", 3 pgs.

"U.S. Appl. No. 12/145,343, Final Office Action mailed Feb. 2, 2012", 12 pgs.

"U.S. Appl. No. 12/145,343, Non Final Office Action mailed Jun. 7, 2012", 13 pgs.

"U.S. Appl. No. 12/145,343, Non Final Office Action mailed Sep. 30, 2011", 10 pgs.

"U.S. Appl. No. 12/145,343, Response filed Apr. 27, 2012 to Final Office Action mailed Feb. 2, 2012", 11 pgs.

"U.S. Appl. No. 12/145,343, Response filed Sep. 7, 2012 to Non Final Office Action mailed Jun. 7, 2012", 11 pgs.

"U.S. Appl. No. 12/145,343, Response filed Dec. 28, 2011 to Non Final Office Action mailed Sep. 28, 2011", 12 pgs.

"Japanese Application Serial No. 2007-525695, Non Final Office Action mailed Oct. 7, 2011", (w/ English translation), 8 pgs.

"Japanese Application Serial No. 2007-525695, Office Action mailed Jun. 20, 2012", (w/ English Translation), 4 pgs.

"Japanese Application Serial No. 2007-525695, Office Action Response filed Jan. 6, 2012", (w/ English translation), 10 pgs.

"Japanese Application Serial No. 2007-525695, Response filed Aug. 27, 2012 to Office Action mailed Jun. 20, 2012", (w/ English translation of claims), 8 pgs.

* cited by examiner

SECURE REMOTE ACCESS FOR AN IMPLANTABLE MEDICAL DEVICE

CROSS-REFERENCE TO RELATED DOCUMENTS

This application is a divisional of U.S. application Ser. No. 10/914,641, filed Aug. 9, 2004, now issued as U.S. Pat. No. 7,890,180, which is hereby incorporated by reference in its entirety.

This document is related to commonly assigned U.S. patent application Ser. No. 10/601,763, filed Jun. 23, 2003, now issued as U.S. Pat. No. 7,155,290, entitled SECURE LONG-RANGE TELEMETRY FOR IMPLANTABLE MEDICAL DEVICE, which is incorporated herein by reference.

This document is related to commonly assigned U.S. patent application Ser. No. 10/801,070, filed Mar. 15, 2004, now issued as U.S. Pat. No. 7,228,182, entitled CRYPTOGRAPHIC AUTHENTICATION FOR TELEMETRY WITH AN IMPLANTABLE MEDICAL DEVICE, which is incorporated herein by reference.

This document is related to commonly assigned U.S. patent application Ser. No. 10/800,806, filed Mar. 15, 2004, entitled SYSTEM AND METHOD FOR SECURELY AUTHENTICATING A DATA EXCHANGE SESSION WITH AN IMPLANTABLE MEDICAL DEVICE, which is incorporated herein by reference.

This document is related to commonly assigned U.S. patent application Ser. No. 10/801,150, filed Mar. 15, 2004, now issued as U.S. Pat. No. 7,475,245, entitled SYSTEM AND METHOD FOR PROVIDING SECURE EXCHANGE OF SENSITIVE INFORMATION WITH AN IMPLANTABLE MEDICAL DEVICE, which is incorporated herein by reference.

TECHNICAL FIELD

This document pertains generally to telemetry for medical devices, and more particularly, but not by way of limitation, to restricting access to selected assets of an implantable device.

BACKGROUND

Implantable medical devices are used to monitor physiological parameters and to deliver therapy to selected organs. An external programmer is often used by physicians to communicate data with an implantable device. The data may include measured parameters, electrocardiograms, markers, instructions, identification information and other such data. Typically, the external programmer includes a near field loop antenna that is positioned near the implantable device and an inductive coupling allows data communications. Because the external antenna is close to the patient, it can be assumed that the programmer is authorized to exchange data with and program the implantable device.

With the advent of far field communications for implantable devices, unauthorized or unintended communications with an implantable device becomes possible. Such communications can result in a minor inconvenience or tragic, life threatening, consequences.

BRIEF DESCRIPTION OF THE DRAWINGS

In the drawings, which are not necessarily drawn to scale, like numerals describe substantially similar components throughout the several views. Like numerals having different letter suffixes correspond to different instances of substantially similar components. The drawings illustrate generally, by way of example, but not by way of limitation, various embodiments of the present subject matter.

DETAILED DESCRIPTION

In the following detailed description, reference is made to the accompanying drawings which form a part hereof and which illustrate specific embodiments of the present subject matter. The various embodiments, which are also referred to herein as examples, are described in sufficient detail to enable those skilled in the art to practice the subject matter, and it is to be understood that the embodiments may be combined, or that other embodiments may be utilized and that structural, logical and electrical changes may be made without departing from the scope of the present subject matter. The detailed description is, therefore, not to be taken in a limiting sense and the scope of the present subject matter is defined by the appended claims and their equivalents.

In this document, the articles "a" and "an" denote both the singular and the plural form of the associated noun, and, unless otherwise noted, the term "or" is used in the non-exclusive sense. Furthermore, all publications, patents, and documents referred to in this document are incorporated by reference herein in their entirety, as though individually incorporated by reference. In the event of inconsistencies between this document and those publications, patents and documents herein incorporated by reference, this document is controlling.

This document refers to a sending device and a receiving device. Unless otherwise provided, the sending device includes either the external device or the implantable device and accordingly, the receiving device includes either the implantable device or the external device, respectively. In other words, at any given time, the external device may be the sending device and the implantable device may be the receiving device and at another time, the device roles may be reversed.

In describing digital data, units of data are variously referred to herein as a packet and a frame. It will be understood that such units of data may differ in the content and the length as well as other parameters. Each such unit of data includes a message. The phrase "data throughput" (or "throughput") refers to the rate at which the message is conveyed between the sending and receiving device.

System Introduction

The present methods and systems control access to an implantable device using one or more security mechanisms tailored to the access needs. One example establishes multiple tiers of a communication session. Each tier is associated with a distinct level of access to one or more assets of an implantable device. The assets of the implantable device include device data as well as processes that can be executed by the device. For example, the ability to access selected memory registers having stored data, the ability to update firmware or software, the ability to program one or more parameters that affect device operation, and the ability to induce a cardiac event (such as a shock or a fibrillation) are all assets. Each of the assets correspond to a potential risk level for the patient. For example, confidential patient and device identification data is stored in certain memory registers. An unauthorized change in firmware or software could endanger the patient. In addition, the ability to induce a cardiac event presents a unique risk that may call for controlled conditions that are available in a properly equipped and staffed medical facility. Consequently, uncontrolled access to various assets of the implantable device poses a risk that can be mitigated by the present systems and methods.

The communication session tiers correspond to distinct levels of access associated with the various individuals requiring access to the implantable device. For example, a technician may have rights to read selected memory registers but has no rights to alter the contents, perform diagnostic testing of the device or program the device. As another example, a following physician may have rights to read all accessible memory locations and may also be allowed to perform diagnostic testing and program certain parameters that affect device operation. The term following physician refers to a physician or other person that provides medical care or monitors device operation.

In addition to granting access rights to an allowed set of assets and preventing access to a prohibited set of assets based on the identity of various individuals requesting access, one example uses one or more security protocols, or mechanisms, to ensure adequate authorization for such access. More rigorous measures are used for higher risk accesses of the device. In one example, the security protocols are keyed to the requested access level.

One example provides remote upgrading or programming of an implantable device. Parameters or software are initially loaded on a temporary basis. If satisfactory results are obtained, the temporary programming is then made permanent. As another example, to program the implantable device from a remote location, the patient (or a proxy present with the patient) provides an input authorizing the programming change. After a desired period of time, the implantable device reverts to a mode that requires another such authorizing input before any requested changes are made. Another example automatically reverts to a mode determined by the last permanently programmed parameters if the communication link is lost or if the session is interrupted.

The present systems and methods are suitable for use with an external device, examples of which include programmers and repeaters. A programmer, in the context of implantable devices, typically includes a display screen, a printer or other output device that conveys data to an operator and receives data or other instructions from a human operator or received from an input interface. A repeater, on the other hand, is typically used for remote monitoring of the implantable device and is also referred to as a remote interrogation device. A remote interrogation device, according to one example, includes a device having an interface to a communication network that enables remote monitoring or programming. The remote interrogation device communicates between the implantable device and the communication network, effectively extending the communication range. For example, a remote interrogation device may be connected to a telephone line within a home thus allowing medical personnel to monitor an implantable device of an occupant of the home via the plain old telephone service (POTS) network. In one example, a remote interrogation device is communicatively coupled to a network such as an intranet or the Internet using a dial-up modem, a broadband connection (including, for example, a cable modem, a digital subscriber line modem or a satellite connection) or other interface.

System Examples

Figure 1:
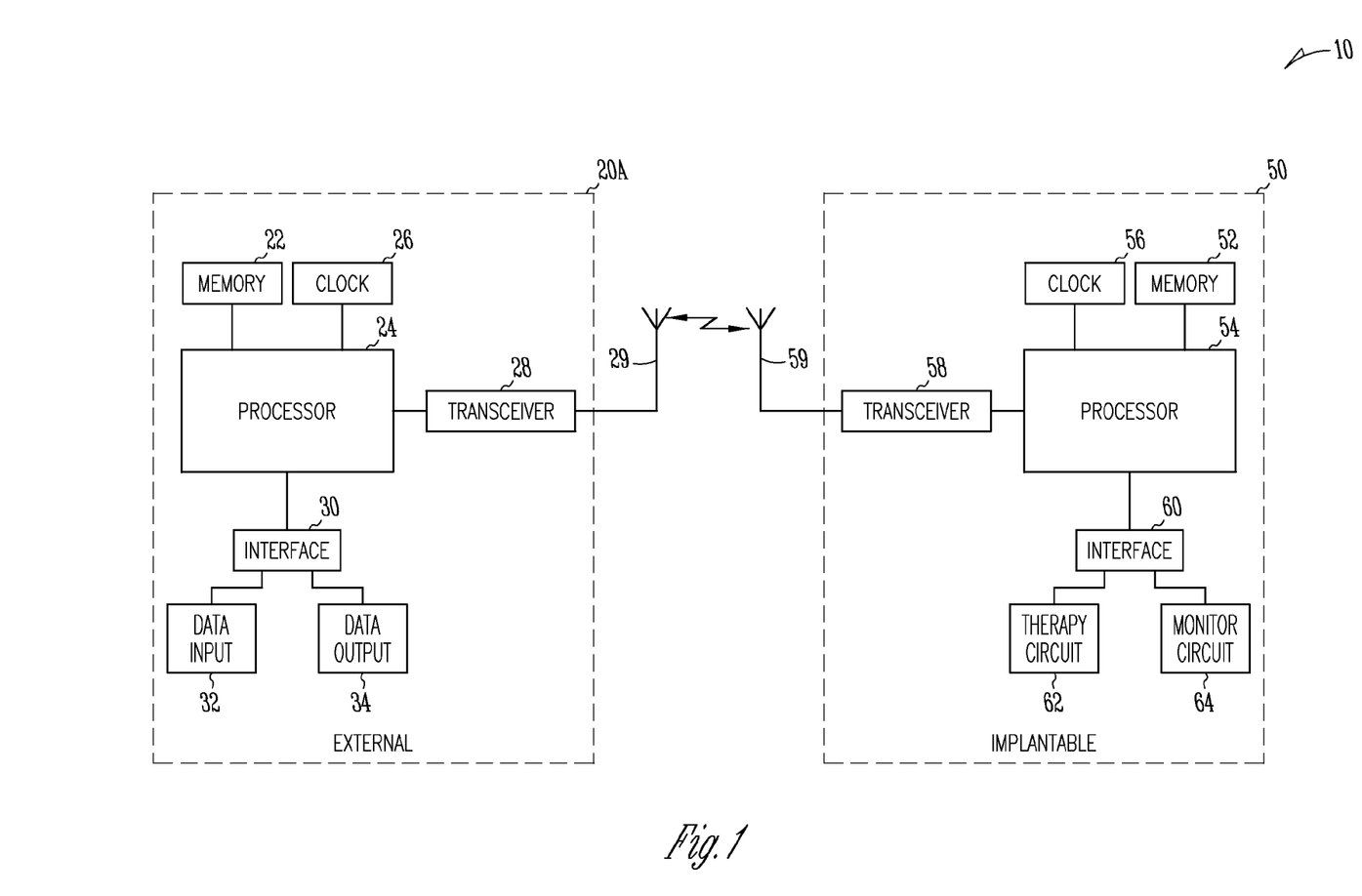
FIG. 1 illustrates an example of a system having an external device and an implantable device configured to communicate wirelessly.

In FIG. 1, system 10 includes external device 20A and implantable device 50 configured for mutual wireless communication.

In this example, external device 20A includes processor 24 coupled to memory 22, clock 26, transceiver 28 and interface 30. Interface 30 is further coupled to data input 32 and data output 34. In one example, the combination of data input 32 and interface 30 is referred to as an input interface and is configured to receive input data for controlling implantable device 50. In one example, the combination of data output 34 and interface 30 is referred to as an output interface and is configured to provide output information based on data units received from implantable device 50.

External device 20A typically implements a remote interrogation device or a programmer. Processor 24, in various examples, is implemented in circuitry to perform signal processing, a microprocessor configured to execute instructions, or any combination thereof. Memory 22 provides storage for instructions or data. Memory 22 includes, in various examples, read only memory, random access memory, removable memory and other types of memory. Clock 26 provides timing signals for processor 24.

Examples of transceiver 28 include a far field radio frequency transmitter and a far field radio frequency receiver. In FIG. 1, transceiver 28 transmits and receives data using far field antenna 29. Data input 32 receives instructions or data for use by external device 20A or implantable device 50. Data input 32, in various example, includes memory, a keyboard, a mouse, a trackball, an optical device, an audio transducer or other data input device. Data output 34 renders data derived from external device 20A or implantable device 50. Data output 34, in various example, includes a printer, a display, a memory and an audio transducer. In one example, data input 32 and data output 34 are combined in a single device. For example, data input 32 and data output 34 use a touch-sensitive screen or a network interface for coupling to a communication network, such as a local area network (LAN, for example, an Ethernet network) or a wide area network (WAN, for example, the Internet). Interface 30 serves as a user interface between data input 32, data output 34 and processor 24. In one example, interface 30 includes a manually operable switch to allow acknowledgement of a message. The above description of external device 20A is not exhaustive and other components or more components are also contemplated. For instance, in one example, external device 20A includes multiple processors 24. External device 20A, in various examples, is powered by a metered line service, a battery, or a telephone loop current.

Implantable device 50 includes processor 54 coupled to memory 52, clock 56, transceiver 58 and interface 60. Interface 60 is further coupled to therapy circuit 62 and monitor circuit 64, each of which can be referred to as an electrical circuit. Implantable device 50, in various example, includes a cardioverter, a cardio defibrillator, a pacemaker, a therapy device or a monitoring device. Processor 54, in various example, is implemented in circuitry to perform signal processing, a microprocessor configured to execute instructions, or any combination thereof. In one example, processor 54 includes circuitry or programming to implement an error detection algorithm. Processor 54 is configured to implement a method as described elsewhere in this document. Memory 52 provides storage for instructions or data, sometimes referred to as data units. Memory 52 includes, in various example, read only memory, random access memory and other types of memory. Clock 56 provides timing signals for implementing a method executed by implantable device 50. Transceiver 58, in the example illustrated, includes a far field radio frequency transmitter and a far field radio frequency receiver, each coupled to far field antenna 59. In one example, transceiver 58, includes a near field radio frequency transmitter and a near field radio frequency receiver, each coupled to near field antenna. Therapy circuit 62 delivers therapy to an organ as a function of a signal received from processor 54. Therapy circuit 62, in one example, includes a pulse generator circuit for delivering electrotherapy. Therapy circuit 62, in one example, includes a drug release circuit for delivering a chemical agent as a function of a signal received from processor 54. Monitor circuit 64, in various example, includes sensors or other devices and circuitry to monitor physiological conditions, parameters or events. Monitor circuit 64, in one example, includes sensors and circuitry to monitor parameters and values associated with implantable device 50. For instance, in one example monitor circuit 64 includes a transthoracic impedance measurement circuit. In one example, therapy circuit 62 and monitor circuit 64 are combined in a single device. Interface 60 serves as an interface between therapy circuit 62, monitor circuit 64 and processor 54. In one example, processor 54 is configured to receive a series of data units from a data source such as, for example, interface 60 (or therapy circuit 62 and monitor circuit 64), clock 56, memory 52 or other data source. The foregoing description of implantable device 50 is not exhaustive and other components or more components are also contemplated. For example, in one example, implantable device 50 includes multiple processors, one of which is illustrated in the figure and described herein as processor 54. Implantable device 50, in various example, is powered by a battery or other energy storage device.

Figure 2A:
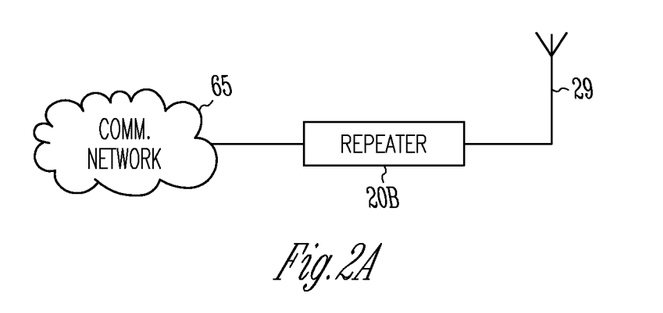
FIGS. 2A and 2B illustrate external devices for use with the present subject matter.

FIGS. 2A and 2B illustrate examples of external devices 20A. In FIG. 2A, the external device is depicted as remote interrogation device 20B and includes antenna 29. Antenna 29 is illustrated as a far field antenna. Remote interrogation device 20B is coupled to communication network 65, such as a public switched telephone network (PSTN), a local area network or a wide area network. In one example, communication network 65 is a wireless communication network. Communication network 65 may include a single or multiple discrete networks.

Figure 2B:
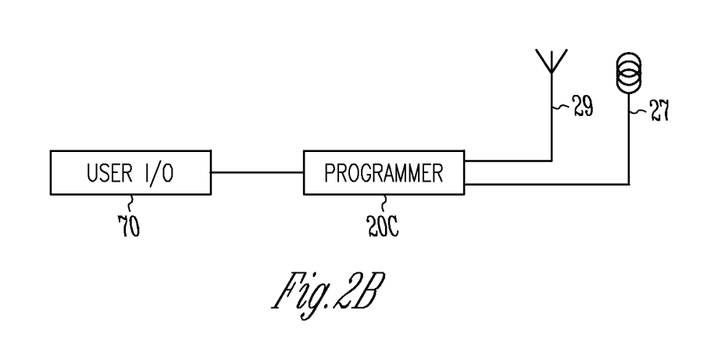

FIG. 2B the external device is depicted as programmer 20C and includes antenna 29 and antenna 27. Antenna 29 is illustrated as a far field antenna. Antenna 27 is illustrated as a near field antenna, and in the example shown, includes an inductive loop antenna. Programmer 20C is coupled to user I/O 70. User I/O 70 includes an input/output interface and, in various examples, includes a keyboard, a mouse, a trackball, a microphone, an optical reader, a touch-sensitive screen, a display screen, a speaker, a printer, a light emitting diode (LED) or other such devices.

Figure 3:
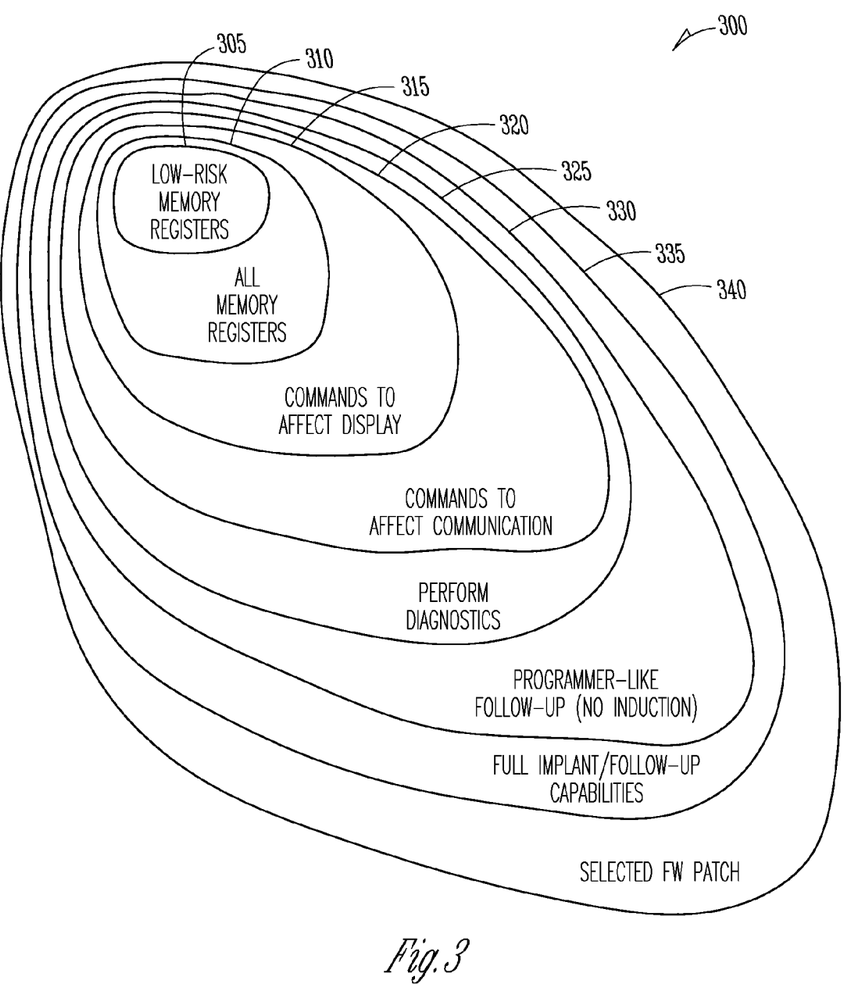
FIG. 3 illustrates a hierarchy of assets.

FIG. 3 diagrammatically illustrates space 300 representing a plurality of assets of an exemplary implantable device. The assets included in space 300 are arranged in order of risk. One end of the spectrum represents reading the contents of relatively low risk data registers. The other end of the spectrum represents the ability to perform routines ordinarily reserved for use by a physician at the time of device implantation. The assets illustrated in space 300 are organized according to one exemplary hierarchy, however other configurations, having different numbers of layers, or tiers, and having a different arrangement of assets are also contemplated.

In space 300, region 305 occupies a central portion of space 300 and represents read-out of low risk memory registers. Such registers are not particularly significant to patient health or privacy, and in one example, includes read-only memory. In one example, region 305 includes registers having content that corresponds to patient health information (PHI). Exemplary patient health information includes device identification, patient identification or information concerning the implantation of the device.

Region 310 permits read-out (without any programming) of other memory registers. For example, region 310 may include all remaining memory registers or a desired subset of all registers. Representative content found in region 310 includes data corresponding to operational parameters or other values which present an elevated risk if access is unrestricted. Region 310 includes region 305.

Region 315 includes commands and instructions that affect a display of data that may be presented on a device coupled to the communication network 65 of remote interrogation device 20B or user I/O 70 of programmer 20C. For instance, in one example, region 315 includes commands that can alter the scale with which data is displayed or depicted. In another example, region 315 includes a function used to select one of a plurality of filters with which data is processed before rendering. Region 315 includes region 310.

Region 320 includes commands and instructions that affect communications between the implantable device and an external device. For instance, in one example, region 320 includes commands that can change the protocol used for communication or that can alter an error checking algorithm. Region 320 includes region 315.

Region 325 includes commands and instructions to perform diagnostics. For instance, in one example, diagnostics include self-tests executed by any combination of the implantable device and the external device. For instance, an exemplary diagnostic routine includes determining the resistance, or integrity, of a lead coupled to the implantable device. In another example, the diagnostic routine evaluates the bandwidth or efficiency of communications with the external device. In one example, a diagnostic routine determines the amplitude of a signal received by the implantable device. In one example, executing a diagnostic routine entails programming or executing a temporary routine. Region 325 includes region 320.

Region 330 includes commands and instructions for performing programmer-like follow-up routines. For instance, an example of a programmer-like follow-up routine includes accessing a selected memory register as well as storing replacement values in selected registers. Region 330 includes region 325.

Region 335 includes commands and instructions to allow for routines executed at the time of device implantation or patient follow up. An exemplary routine performed at the time of implantation includes configuring the device with default values for selected parameters. The default configuration can be altered remotely by the assets of region 340. Region 335 includes region 330.

Region 340 includes commands and instructions to allow for remote installation of a software or firmware patch or upgrade. The patch can includes instructions for controlling a selected routine executed by the implantable device. For instance, one example of a firmware patch, includes a set of instructions that, when executed, provide improved battery monitoring functionality which enhances a physician's ability to estimate device performance. Other patches or software modules are also contemplated. Region 340 includes region 335.

As noted above, the device assets illustrated in space 300 are arranged in an order corresponding to patient risk. For example, the ability to read the contents of the selected memory registers tends toward the benign end of the spectrum whereas, the ability to perform a full implant or follow-up functions may pose a considerable risk for the patient. Other configurations are also contemplated, including more or fewer regions as well as different arrangement of regions.

TABLE 1

| Asset | Description |
| --- | --- |
| Read/Write logical memory | Process that allows an external device to instruct the implantable device to return/write data from/to a logical address space that maps to a constraint set of physical address space. |
| Read/Write physical memory | Process that allows an external device to instruct the implantable device to return/write data from/to some physical address space that is accessible by the microprocessor. |
| Read History | Process that allows an external device to instruct the implantable device to return the contents of a patient's therapy history. |
| Commanded Action | Process that allows an external device to either initiate some action or change the state of the implantable device. |
| System Identification | Logical block that includes unique data that identifies the implantable device, such as its model number, serial number, or timestamp that relates to when it was manufactured. |
| Detection (event or condition) | Logical block that includes multiple parameters that can affect detection therapy. |
| Device Configuration | Logical block that includes multiple parameters that can enable implantable device specific configurations for partitioning episode memory storage, enabling beeper on certain faults, etc. |
| Device History | Memory address space that includes the patient's therapy history (episode data and treatment). |
| Therapy | Logical block that includes multiple parameters that can affect the delivery of therapy. |
| Calibration | Logical block that includes calibration constants specific to an implantable device. |
| Patient Data | Logical block that includes individual patient personal information. |
| Fault Conditions | Logical block that is reserved for internal faults detected by the implantable device. |
| Hardware Registers | Memory address space that provides the interface from the firmware to the microprocessor. |
| RAM Code | Memory address space that includes the device executable firmware code. |

Table 1 enumerates selected assets of an exemplary implantable device. An asset can include a particular block of data, such as patient or device information, or a method, such as a process for delivering an inducing pulse to a heart. In one example, some processes or methods are configured to act on a limited set of data while other methods are more generic and can act on any data. In one example, a process such as a commanded shock, allows a user to directly apply therapy to the patient without accessing any data. Other assets are also contemplated.

TABLE 2

| Hierarchy | Access Control |
| --- | --- |
| Tier 1 | read only commands to selected memory in the PG |
| Tier 2 | limited to commands that affect display or communication actions |
| Tier 3 | limited commands to run diagnostic tests |
| Tier 4 | most commands supported by a PRM during a regular patient follow-up; changing programmable parameters |
| Tier 5 | all commands supported by the PRM during a regular patient implant/follow-up; includes fibrillation induction |
| Tier 6 | limited software uploads |

Table 2 illustrates an example of session tier hierarchy wherein six tiers are depicted. Each tier is associated with an array of assets as illustrated in the table. As noted, when operating according to Tier 1, the level of access afforded includes executing read only commands to determine the contents of selected memory in the implantable device, herein referred to as a pulse generator (PG). At Tier 2, the implantable device will execute a limited set of commands, from a plurality of commands, which affect either the display on a programmer or a communication action. For example, a display scale of an electrocardiogram can be set using a Tier 2 access. In addition, under Tier 2, the implantable device can be configured to transmit data in a particular manner or processed through a particular filter function before transmitting the data. When operating according to Tier 3, a limited set of commands are available that can be used to execute diagnostic routines. For example, a test to generate a series of intrinsic measurements can be executed from Tier 3. As another example under Tier 3, a temporary operational parameter can be installed and evaluated. When operating according to Tier 4, an implantable device will respond to a larger subset of commands including those supported by an external programmer (PRM) during a regular patient follow-up visit. By way of example, under Tier 4 a remote follow-up visit can be performed using a remote interrogation device or a programmable parameter can be changed. While operating under Tier 4, one example precludes inducing fibrillation in a patient. When operating according to Tier 5, all commands supported by an external programmer, such as those executed during an implantation procedure, are available and device assets that not accessible to a regular physician are not available. For instance, under Tier 5, a physician cannot download software to the RAM module or have access to internal data collected by the device. Under Tier 5, for example, fibrillation can be induced since that would be allowable during a normal implant procedure. In Tier 6, a limited amount of software or firmware can be uploaded to the implantable device. For example, a firmware patch can be installed while operating under Tier 6. In one example, different security protocols are associated with each of the different tiers.

Larger or smaller numbers of tiers are also contemplated for alternative examples.

Session Based Remote Access Control Table

Access control for an example of the present subject matter can be depicted as shown at Table 3. The table is prepared from the perspective of the implantable device. The entries in the table are representative and can include other implantable device-remote interrogation device pair mechanisms such as for example, protocol or hardware based. For instance, an access card or a token can be used to identify a user and thus establish access credentials. The initiation requirements column refers to what mechanisms are used to initiate a communication session. In the column, wakeup AC refers to an access control that triggers the device to respond to a far field, or near field wake-up signal. In the security mechanism column, an example of a protocol-based integrity check includes a cyclic redundancy check (CRC) code. In addition, a message digest code, as associated with a hash function can also be used to implement a protocol-based integrity check. The column marked role credentials provides the minimum credentials needed to operate at the particular tier. The credentials are enforced by a server coupled to the remote interrogation device or a programmer or the implantable device. Exemplary credentials include those of a technical support person, a researcher, a medical professional, a following physician and a manufacturer's representative. For example, a technician account can be established in a hospital which includes the credentials to read data from a particular implantable device. Thereafter, the technician can access the selected assets of the device remotely.

TABLE 3

| Class | Initiation requirements | Remote Access Authorization | Security Mechanism | Role Credentials |
| --- | --- | --- | --- | --- |
| Tier 1 | Wakeup AC | 1. Read Access | 1. Encryption of selected confidential data<br>2. Protocol based integrity checks | 1. Technical Support<br>2. Researcher<br>3. Medical Professional<br>4. Following Physician |
| Tier 2 | Wakeup AC | 1. Read Access<br>2. Update access to limited parameters that affect how data from Tier 1 is displayed (e.g. EGM scale) | 1. Encryption of selected confidential data<br>2. Protocol based integrity checks<br>3. Message Authentication | 1. Technical Support<br>2. Researcher<br>3. Medical Professional<br>4. Following Physician |
| Tier 3 | Wakeup AC | 1. Read Access<br>2. Update access to limited parameters that affect how data from Tier 1 is displayed (e.g. EGM scale)<br>3. Run device diagnostics | 1. Encryption of selected confidential data<br>2. Protocol based integrity checks<br>3. Message Authentication | 3. Medical Professional<br>4. Following Physician |
| Tier 4 | Device placed over PG to convey consent (e.g. Patient Activator) | Programmer-like follow-up capabilities. Induction schemes prohibited | PKI or similar technology that supports identification, confidentiality, authentication, integrity and non-repudiation | 4. Following Physician |
| Tier 5 | Programmer with a telemetry wand | full implant/follow-up capabilities | 1. Encryption of selected confidential data<br>2. Protocol based integrity checks<br>3. Message Authentication<br>4. Remote access only with a programmer and after wand is waved over the patient | Implant/Following Physician |
| Tier 6 | Device placed over PG to convey consent (e.g. Patient Activator) | 1. Programmer-like follow-up capabilities. Induction schemes prohibited.<br>2. Limited FW patch upload and test capability. Only used for extreme cases when the risk to have the issue is higher than the risk of uploading a patch remotely and a specific patient cannot get to a clinic. | 1. PKI or similar technology that supports identification, confidentiality, authentication, integrity and non-repudiation<br>2. Both manufacturer's representative and Following Physician roles must be signed into the system to approve before action takes place. | 4. Following Physician along with manufacturer's representative |

As noted in Table 3, those assets denoted as "read" allow access to a selected number of implantable device memory registers. In one example, certain constraints may be imposed to protect security mechanisms for higher session tiers.

In addition, the asset "update" indicates that there is a write action to the implantable device and therefore, potential regulatory implications apply to the classification of the hardware (for example, a remote interrogation device) that allows this level of access.

Table 3 indicates that more than one set of credentials are required to conduct a Tier 6 communication session. As noted in the example, a physician, such as an electro physiologist, and a manufacturer's representative are required to enter their credentials to allow access to the assets of Tier 6.

In one example, Tier 1 and Tier 2 are combined since both present little or no risk and the same user role can be allowed to perform these actions during the same session. By having Tier 1 separate from Tier 2, however, the security mechanisms can be differentiated with those associated with Tier 2 configured with more stringent requirements.

In the table, the role credentials are associated with increasing levels of access to the system based on their credentials. It is noted that the table illustrates but one example and other configurations or numbers of tiers, and associated assets, security mechanisms and role credentials are also contemplated.

Figure 4:
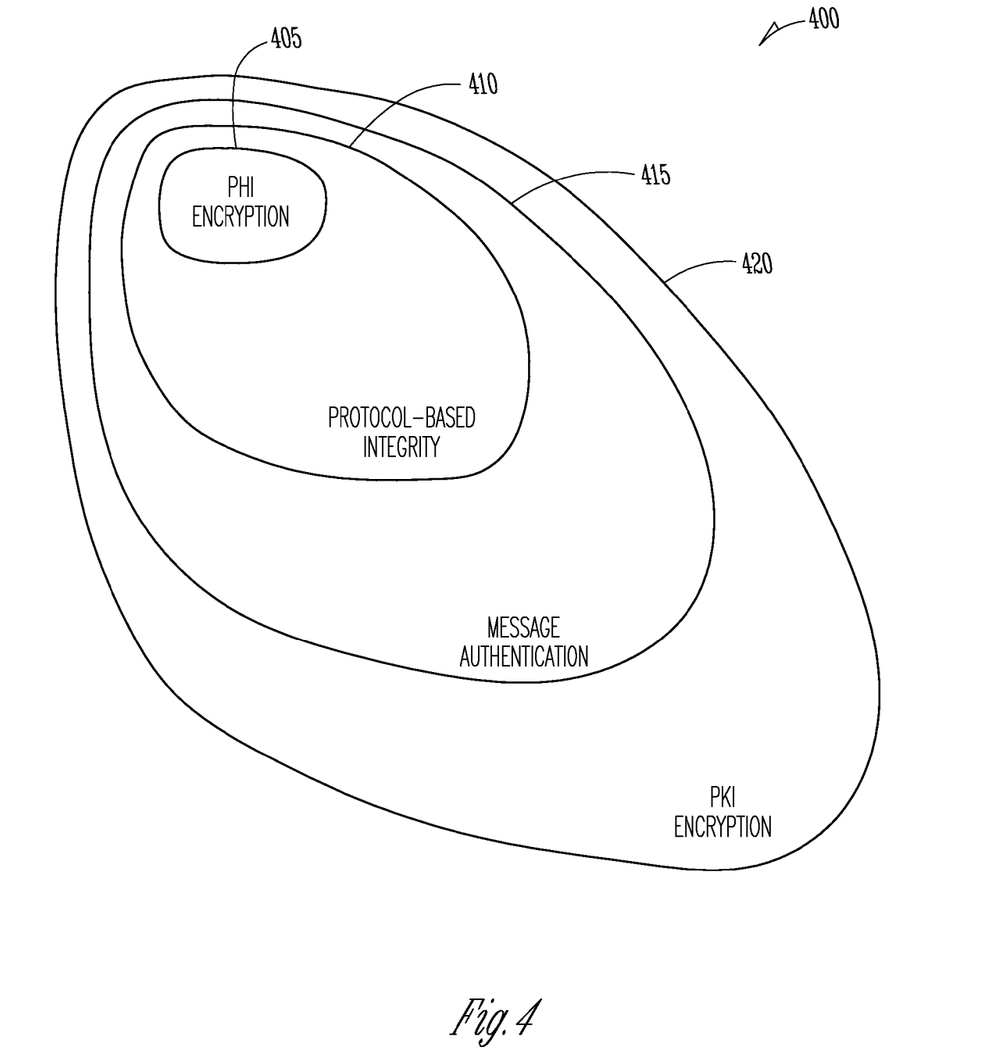
FIG. 4 illustrates a hierarchy of security mechanisms.

FIG. 4 illustrates a hierarchical, or tiered arrangement of security measures that are overlaid with the device assets. In other words, for communications conducted using lower risk assets, as illustrated in FIG. 3, a security measure applied to protect those assets may be less robust than a security measure applied to protect a higher risk assets. For the higher risk assets, a more complex security measure is applied. With increasing complexity of the security measure, the burden on the processor is increased and thus the device longevity may be reduced.

In space 400, for example, an encryption or other security routine, such as that used with patient health information, is applied to communications involving corresponding device assets as depicted at region 405. Encryption may include a symmetrical or asymmetrical encryption algorithm or other routine to safeguard selected data, including, for example, patient health information.

In region 410, the security measure applied to communications involving corresponding assets include a communication protocol-based integrity mechanism. For example, a protocol-based integrity mechanism can include a cyclic redundancy code check, specific header encoding bits and other protocol based mechanisms.

At region 415, communications concerning the corresponding assets are secured using a message authentication routine or algorithm. The message authentication routine provides a mechanism to establish that the message originated from the sending party. The message authentication routine is able to detect if the message has been altered after it is transmitted. An example of a message authentication routine includes a presumptively one way algorithm that is used to generate a message digest at both the sending and receiving ends of the communication link. If the message has been altered, the message digest returned by the one way algorithm will reveal a detectable difference. Other message authentication routines are also contemplated. In one example, a cryptographic security algorithm is executed by the implantable device.

At 420, a public key encryption algorithm is applied for communications associated with higher risk assets. Public key infrastructure (PKI) or encryption, also referred to as asymmetrical encryption refers to a routine involving two keys, one of which is public and the other is private. A message encrypted with the public key can be deciphered using the private key.

Other security mechanisms may also be applied and arranged in a different order. As noted, the more robust security routines are applied to communications involving the higher risk assets and less robust routines are applied to communications involving low risk assets. Other configurations are also contemplated, including for example, a single security routine applied to communications involving all assets without regard for the level of risk. In one example, the security mechanism provides identification, confidentiality, authentication and non-repudiation protection.

Method Examples

Figure 5A:
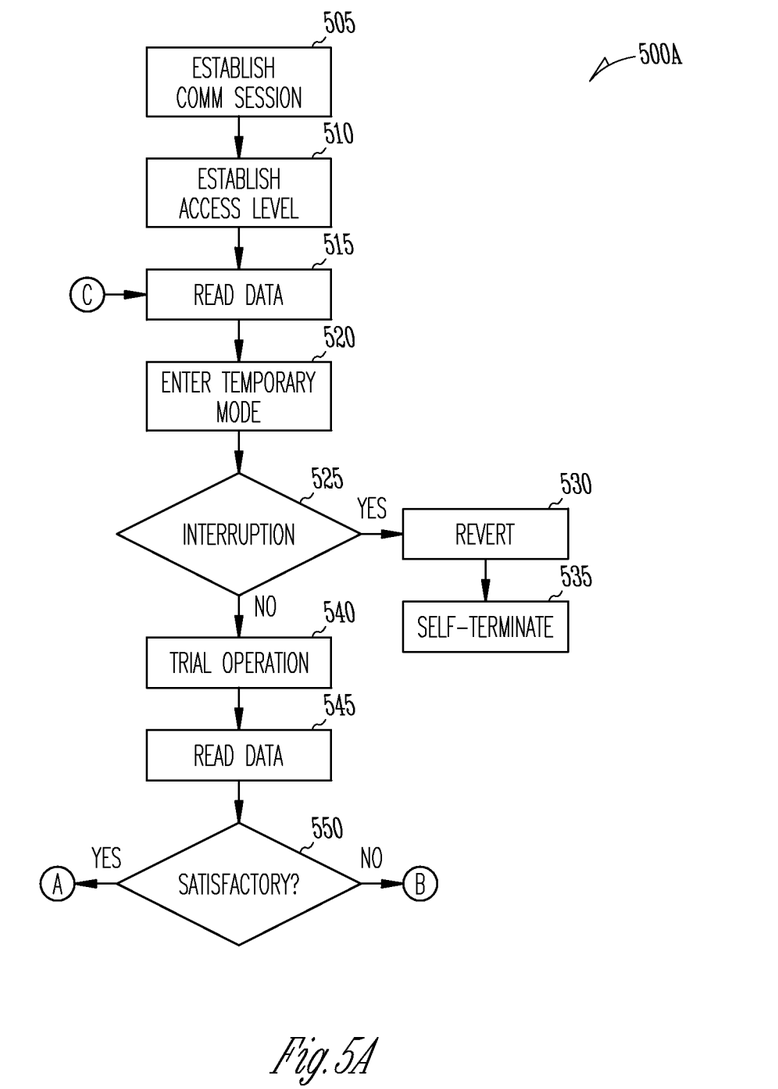
FIGS. 5A and 5B illustrate a flow chart of a method of communicating with an implantable device.
Figure 5B:
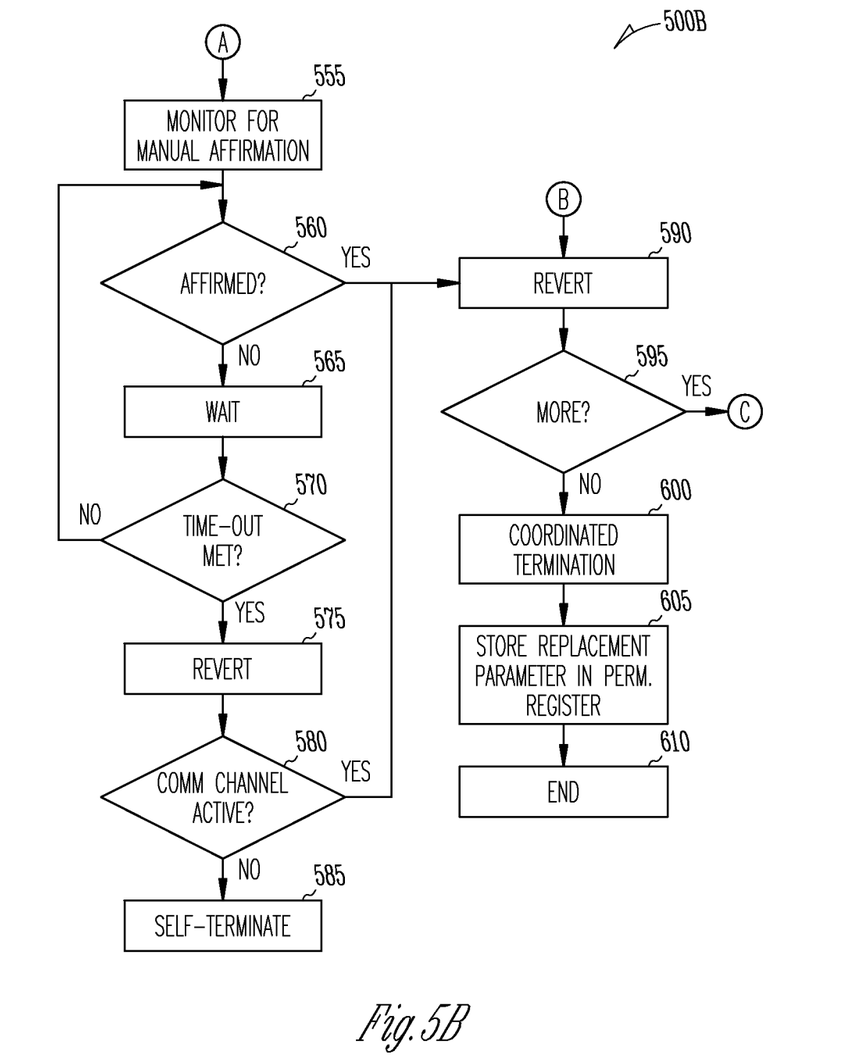

A flowchart of a method executed by an exemplary system is illustrated in FIGS. 5A and 5B. FIGS. 5A and 5B illustrate routines 500A and 500B, respectively, and depict a routine whereby data is read from the implantable device and a replacement parameter or instructions are uploaded to the device.

At 505, a communication session is established between an external device and an implantable device. The external device may include a programmer or a remote interrogation device in communication with a remote server. The implantable device, in various examples, includes a cardioverter, a pacemaker, a defibrillator, a cardiac monitor, or other such device. The communication session can be established, or initiated, by using a far field telemetry link or a near field telemetry link.

At 510, an initial level of access is established. The level of access prescribes the particular assets that are available during the session. In one example, the available assets depend on how the communication session is initiated. For example, if a near field telemetry link, such as an inductive loop antenna, is used to initiate the communication session, then it is reasonable to presume that the external device includes a local programmer, rather than a remote interrogation device. This triggers the ability to access higher level assets. In one example, if the communication session is initiated using a far field telemetry system, other mechanisms are employed to establish the level of access available in the communication session. In one example, the external device prompts an operator to enter an access code that denotes the level of access available to that operator. A technician, for example, may enjoy lower level access than that of a following physician. The user entered access code can be provided by a user using a keyboard, a mouse, a cursor control, a storage device or other mechanism. In one example, the user entered access code determines the communication mode and thus, the implantable device assets that are accessible to that user.

Following initiation of the communication session and establishment of an access level, the illustrated example provides that selected device data is read at 515. As noted, all access levels enjoy access to a selected set of memory registers but access to higher level assets is restricted based on the access level established in an earlier routine.

In the illustrated example, at 520, a temporary mode is established to allow for trial application of a new parameter or programming. In one example, the temporary mode is initiated by sending a particular code to the implantable device.

At 525, the implantable device monitors and evaluates the communication link to determine if an interruption has occurred. If the communication link has been interrupted, for example, by noise or by a weak signal, then the method proceeds to 530 where any earlier changes in programming, parameters or memory contents are restored and the device reverts to an earlier mode of operation. In one example, a safeguard protects against interruptions by using a temporary program mode where changes are automatically reversed and the device is returned to a previous configuration. The previous configuration may include the most recent or permanent state or a default state. In addition, the implantable device executes a self-termination routine, at 535, to clean up any incomplete processing and resume normal operation. In one embodiment, the inquiry at 525 is performed at all stages of the method however, for sake of clarity, it is shown in the single location noted in FIG. 5A.

Assuming that the communication link remains viable and has not been interrupted, then at 540, a trial operation is commenced. In one example, this includes receiving replacement data, such as a parameter or programming instruction and executing a routine that accesses the replacement data. The replacement data at 540 is applied on a temporary basis.

At 545, other data, such as that derived from the implantable device or other sensor, is read. At 550, a query is presented to determine if the patient or device is performing satisfactorily. A variety of evaluation measures may be considered in determining if the trial operation is an improvement over the prior configuration. If the trial operation is satisfactory, then processing proceeds, via label A, to a corresponding portion of routine 500B illustrated in FIG. 5B. If the trial operation is unsatisfactory, then processing proceeds, via label B, to 590 where the implantable device reverts to a previous configuration followed by a query at 595 to determine if the communication session is to continue.

With satisfactory trial operation, then at 555, the implantable device monitors for manual affirmation or acknowledgement of the trial configuration. In one example, this includes monitoring for activation of a button corresponding to acceptance of the trial configuration. The button, or switch, may be activated by a patient or by a patient advocate that is present during the communication session. Activation of the switch denotes acknowledgement or approval of the new settings. In effect, two actions are required to invoke a change in a device setting: first the change is requested; and second, a manual affirmation is required to apply the change.

If manual affirmation is detected, processing continues to 595 where a query is presented to determine if the communication session is to continue. If manual affirmation is not detected, then, after waiting period 565, a query is presented to determine if a predetermined time-out value has been met at 570. If the time-out value has not been met, then the process loops to 560 where the affirmation query is again presented. If the time-out value has been met, then the implantable device reverts, at 575, to a previous configuration and the trial configuration is no longer executed. In addition, at 580, if the communication channel has been disabled, then at 585, the implantable device executes the self-termination routine. If, on the other hand, the communication channel remains active, then processing proceeds to the query at 595 to determine if the communication session is to continue.

Following the query at 595, a negative answer will cause processing to continue to 600 where the communication session is terminated in a coordinated manner by executing a predetermined routine of handshaking. In addition, at 605, a trial configuration, which was previously executed on a temporary basis, is shifted into a permanent register. The implantable device continues to operate on the basis of the permanent configuration until further changes are made. The method and the communication session are terminated at 610.

Prior to executing the method of FIGS. 5A and 5B, or in conjunction with that method, in one example, the device assets and the particular interfaces to those assets are identified. The device assets are deemed to pose a risk to the patient. In addition, one example provides that a tier-based session class is defined which determines access control mechanisms to establish and maintain a communication session with the implantable device.

In one example, an array of security mechanisms are associated with the multiple tiers associated with the device assets. The array of security mechanisms may include a single mechanism or multiple mechanisms arranged with increasing level of security with increasing level of risk posed to the patient. The security mechanisms are applied in proportion to the session class being requested.

In one example, a remote interrogation device initiates a session at a Tier 1 level with a particular implantable device. This allows for wake-ups and synchronization. The implantable device acknowledges Tier 1 access as read-only access to selected memory registers. The implantable device allows access on a message-to-message basis if the messages from the remote interrogation device satisfy all the integrity checks and also meets the wake-up access code recorded in the implantable device at the time of manufacturing. In one example a predetermined message from the remote interrogation device, when received by the implantable device, allows the remote interrogation device to request a higher level of access.

Figure 6:
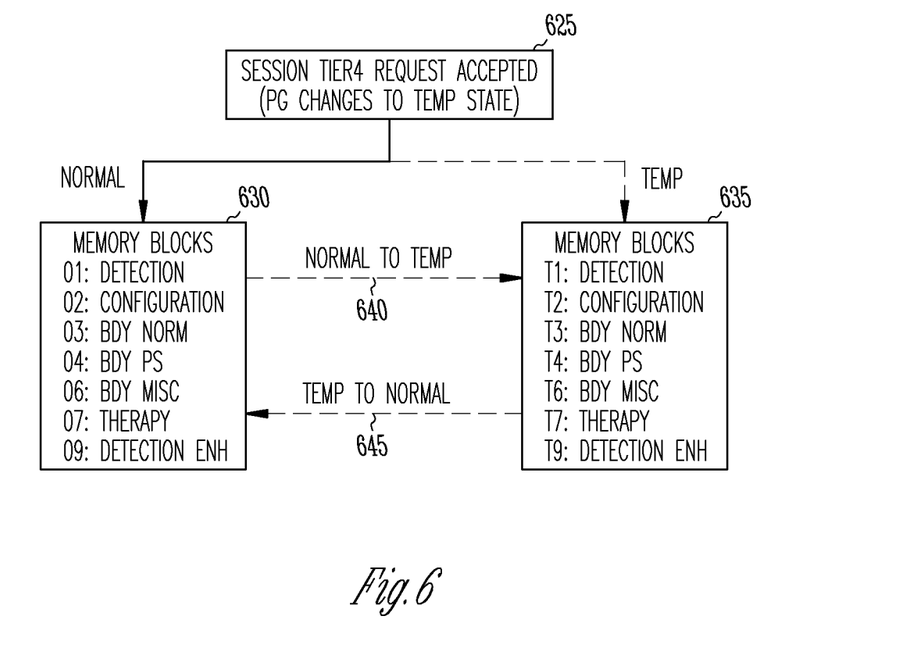
FIG. 6 illustrates an example of remote update safeguards.

FIG. 6 illustrates how the implantable device transitions from a normal mode to a temporary mode and then returns to the normal mode. If an affirmation is not received or if the session is interrupted or prematurely ends, then the implantable device automatically reverts to the normal (or previous) configuration. As illustrated, at 625, a communication session at Tier 4 has been accepted and is in process. Assets 630, depicted as an array, are identified with each element corresponding to a particular block of memory. The contents of assets 630 are those stored while in a normal mode. At 635, the array of assets is configured with temporary contents. Arrow 640 indicates the transition from a normal operating mode to a temporary, or trial configuration. The implantable device will automatically revert to the normal mode, as shown by arrow 645 in the absence of an affirming instruction to make the temporary contents operable permanently.

Other Examples

In one example the communication session is initiated using a wand having an inductive coupling. In one example, a security mechanism or access control mechanism is combined with the wand initiated session. For instance, one example provides that the implantable device discriminate between a programmer and a remote interrogation device. The procedure followed to initiate the session can be used to discriminate between devices, namely, a wanded session initiation is associated with a programmer and a remote interrogation device session is initiated by other means.

In one example, access to the implantable device asset (which can include information or actions) can be controlled in a remote environment based on a session tier approach. The device assets are categorized based on a risk assessment. Any operations available on the implantable device for each asset or group of assets is identified. An exemplary list of session tiers with increasing access control requirements and security technology requirements is as follows:

Tier 1: read-only to most implantable device memory registers

Tier 2: Tier 1 plus adjust display on an external device

Tier 3: Tier 2 plus program diagnostic parameters

Tier 4: Tier 3 plus program therapy parameters

Tier 5: Tier 4 plus full remote programmer capabilities

Tier 6: Tier 5 plus read/write access to any device assets and includes non-restrictive access to any assets in the implantable device.

In one example, remote programming at or above a particular tier includes a safety mechanism by which interruption of remote communication reverts the device to a previous state. For instance, in one example, a revert mechanism is applied for communications conducted at or above Tier 3.

In one example, medical data and identification information is treated differently within the implantable device. For instance, in one example, patient health information is encrypted and identification information remains in plaintext.

In one example, the implantable device does not include an encryption or decryption module and it is the external device that encrypts and decrypts the data. As such, the external device encodes and decodes the data and transfers it to the implantable device for storage in a memory register.

In one example, two tiers are established in an implantable device. For instance, one example provides that a first set of assets (such as reading selected memory registers) are remotely readable using a remote interrogation device and a server and a second set of assets (such as performing patient follow-up routines) are available using a programmer with a wand. In one example, the implantable device includes a plurality of antennas for receiving and transmitting.

In one example, a session is initiated using an inductive link. In one example, a far field signal, such as a radio frequency signal, is used to initiate a communication session. For example, the implantable device ordinarily performs a wake-up routine on a periodic basis, such as once per minute. If, during the wake-up routine, the implantable device detects and recognizes a particular protocol, then the implantable device suspends the wake-up duty cycle routine and remains alert for further communication. If further communications are received, then the implantable device enters a Tier 1 communication session. Thereafter, the implantable device allows access to those assets classified as accessible while operating under Tier 1.

In one example, if the implantable device detects and recognizes the presence of an inductive wand, then following a handshaking routine, the implantable device wakes up and enters a Tier 5 communication session. All assets available under Tier 5 are then accessible for the duration of the session or until the session tier is changed.

In one example, the particular communication session tier is based on the manner of initiating the session. The manner of initiating the session is interpreted by the implantable device as a tier selection signal. In one example, the particular communication session tier is based on a message or signal that is telemetered to the implantable device by the external device. For example, the message can include a key or other predetermined code. In one example, the message includes a challenge and trust is established upon providing the correct response. The correct response, in one example, includes a synchronized token identification code that periodically changes values. The token identification code can be blended with a password to generate a unique result that can be calculated by the remote interrogation device.

In one example, the external device requests data from the implantable device and the implantable device serves as a gatekeeper. As a gatekeeper, the implantable device determines what data is to be transmitted, in response to the request, and as a function of the session tier.

In one example, a mechanism is provided to transition from one tier to another tier in a hierarchy. For instance, in one example, a code word or other data exchange sequence will trigger an increase or decrease in the access level. In one example, a transition in sessions is conducted by terminating one session and initiating a second session. In various examples, the request to transition is sent in encrypted or plaintext. Upon receiving a request to transition to an increased level of access, the implantable device executes a routine to check authorization of the credentials before the change is made. In one example, the access levels are cumulative in that higher levels include the rights to access assets of lower levels.

In one example, a person can establish a communication session at a level below that of their credentials. For example, a following physician may opt to initiate, or request transition to, a Tier 1 communication session and yet the physician is authorized to conduct a Tier 6 communication session.

In one example, the duration of a temporary or trial configuration is selectable. For instance, in one example, a physician may opt to engage a trial configuration for a period of seconds or for a period of days to allow a full evaluation before engaging the configuration permanently. After the trial period has expired the implantable device automatically reverts to a previous configuration.

It is to be understood that the above description is intended to be illustrative, and not restrictive. For example, the above-described embodiments, or any portion thereof, may be used in combination with each other. In the appended claims, the phrase "any combination" includes a single element as well as multiple elements. Furthermore, the transitional terms comprising and including are used in the open ended sense in that elements in addition to those enumerated may also be present. Other embodiments will be apparent to those of skill in the art upon reviewing this document.

What is claimed is:

1. A system comprising:
an external device including:
a transceiver configured to wirelessly communicate with an implantable device; and
a user interface configured to configured to receive a user-entered access code;
an implantable device including:
a processor;
an electrical circuit coupled to the processor;
a transceiver coupled to the processor and configured to wirelessly communicate with an external device; and
a memory accessible to the processor and having instructions stored thereon for implementing a plurality of communication session modes, a particular communication session mode associated with the user-entered access code and wherein a first mode is associated with a first set of one or more implantable device assets and a second mode is associated with a second set of one or more implantable device assets and wherein the first set and second set are different,
wherein, while in the first mode, the processor is configured to:
receive a request for access to the first set of assets, wherein a security protocol is applied in the first mode to a communicated request according to the user access code, wherein the security protocol is one of a plurality of security protocols have varying different levels of complexity according to a level of potential risk posed to patient health by the access to sets of assets;
permit access to the first set of assets when the security protocol meets a level of security required to access the first set of assets; and
prevent access to the first set of assets when the level of security of the security protocol does not meet the level of security required to access the first set of assets.

2. The system of claim 1, wherein the first set of assets includes at least one executable process.

3. The device system of claim 1, wherein the user-entered access code denotes a level of access to implantable device assets available to an operator of the external device.

4. The system of claim 1, wherein the electrical circuit includes at least one of a therapy circuit configured to deliver therapy to an organ and a monitor circuit configured to monitor at least one of a physiological parameter and a device parameter.

5. The system of claim 4, wherein the therapy circuit is configured to deliver an electrical pulse.

6. The system of claim 1, wherein a communication session mode is determined by a signal received by the transceiver.

7. The system of claim 6, wherein the signal is received upon initiation of a communication session.

8. The system of claim 6, wherein the first mode is instantiated upon receiving a first signal and the second mode is instantiated upon receiving a second signal.

9. The system of claim 6, further including:
a near field antenna coupled to the transceiver; and
wherein the first signal is received by the near field antenna.

10. The system of claim 6, further including:
a far field antenna coupled to the transceiver; and
wherein the second signal is received by the far field antenna.

11. The system of claim 6, further including:
a near field antenna; and
a far field antenna; and
wherein a communication session initiated by the near field antenna triggers the first mode and a communication session initiated by the far field antenna triggers the second mode, wherein the second mode has a more restrictive security protocol than the first mode.

12. The system of claim 1, wherein the processor is configured to receive, as the request for access to the first set of assets, at least one of:
a request to access an asset that affects communications with the implantable device;
a request to execute a diagnostic test; and
a command for uploading software.

13. The system of claim 1, including a first receiving antenna and a second receiving antenna, wherein the first communication session mode uses the first receiving antenna and the second communication session mode uses the second receiving antenna.

14. The system of claim 1, wherein the processor is configured to receive an encrypted request for access to the first set of assets.

15. The system of claim 1, wherein the plurality of security protocols includes at least one of a public key infrastructure (PKI) algorithm, a message authentication algorithm, and a non-repudiation algorithm.

16. The system of claim 1, wherein the processor is configured to receive a request to change the implantable device from a first configuration to a second configuration, wherein the first configuration differs from the second configuration.

17. The system of claim 16, wherein the processor is configured to implement the change by storing at least one parameter in a temporary memory register and operating the device according to the stored parameter.

18. The system of claim 17, wherein processor is configured to store the parameter in permanent memory following a command received from the external device in the first communication session mode.

19. The system of claim 16, wherein the processor is configured to revert the implantable device to the first configuration when the communication session is interrupted.

20. The system of claim 1, wherein the transceiver is configured to receive the user-entered access code from the external device, and wherein the first set of assets is identified by the access code.

* * * * *